United States Patent [19]

Cais et al.

[11] Patent Number: 4,645,747

[45] Date of Patent: * Feb. 24, 1987

[54] SPECIFIC BINDING ASSAY TECHNIQUE

[75] Inventors: Michael Cais; Moshe Shimoni; Abraham Baniel, all of Haifa, Israel

[73] Assignee: Technion Research & Development Foundation, Ltd., Technion City, Israel

[ * ] Notice: The portion of the term of this patent subsequent to Jun. 12, 2001 has been disclaimed.

[21] Appl. No.: 470,334

[22] Filed: Feb. 28, 1983

Related U.S. Application Data

[63] Continuation-in-part of Ser. No. 124,691, Feb. 26, 1980, abandoned.

[30] Foreign Application Priority Data

Mar. 11, 1979 [IL] Israel .......................................... 56389

[51] Int. Cl.$^4$ .................. G01N 33/537; G01N 33/538
[52] U.S. Cl. ..................................... 436/500; 436/538; 436/542; 436/541; 436/807; 436/816; 436/817; 436/824
[58] Field of Search ........................... 435/4, 5, 7, 810; 436/500, 536, 538, 541, 542, 545, 804, 824, 815, 816, 817, 826, 807

[56] References Cited

U.S. PATENT DOCUMENTS

| | | | |
|---|---|---|---|
| 4,125,375 | 11/1978 | Hunter | 436/518 |
| 4,220,450 | 9/1980 | Maggio | 435/7 |
| 4,301,139 | 11/1981 | Feingers et al. | 422/61 |
| 4,312,944 | 1/1982 | Mattiasson | 435/7 |
| 4,454,231 | 6/1984 | Cais et al. | 436/500 |
| 4,456,690 | 6/1984 | Cais et al. | 436/500 |

OTHER PUBLICATIONS

Jowett et al, Clin. Sci Mol. Med., 45: 607–623 (1973).
Parker, *Radioimmunoassay of Biologically Active Compounds,* Prentice-Hall, Inc., Englewood Cliffs, N.J., 68–71 (1976).
Cason, *Laboratory Text in Organic Chemistry,* 2nd edition, Prentice-Hall, Inc., Englewood Cliffs, N.J., 259–261 (1962).

*Primary Examiner*—Esther M. Kepplinger
*Attorney, Agent, or Firm*—Schwartz, Jeffery, Schwaab, Mack, Blumenthal & Evans

[57] ABSTRACT

The present invention relates to a simple and accurate method to be applied in immunoassay technique for separating the free ligand from the antibody-bound ligand.

The method involves the use of a solvent extraction operation which at equilibrium provides the formation of two distinct phases the free- and bound-fraction. The solvent to be utilized should be slightly water miscible or completely water immiscible, having the property of marked selective extraction power toward the gamma-labelled constituent to be determined. The method is applicable in a liquid-liquid system, a solid-liquid system and solid-solid system.

The method is useful for radioimmunoassay, free radical assay or metallo-immunoassay, being most versatile having also the advantage that as a result of the free ligand being extracted into the solvent, the determination of the quantity of gamma-labelled substance in the free and/or bound fraction compares very favorably with the known prior art methods in immunoassays.

14 Claims, 4 Drawing Figures

Figure 1:
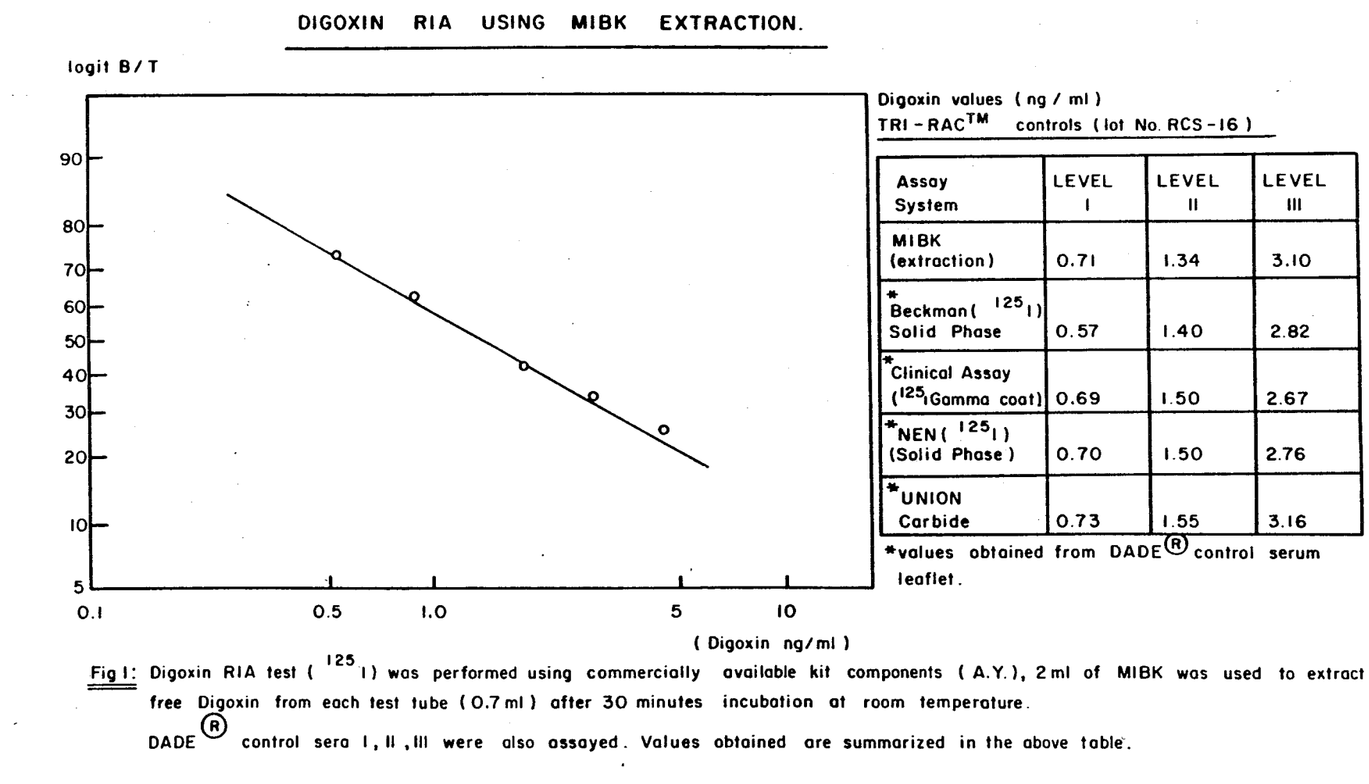

Fig 1: Digoxin RIA test ($^{125}I$) was performed using commercially available kit components (A.Y.), 2 ml of MIBK was used to extract free Digoxin from each test tube (0.7 ml) after 30 minutes incubation at room temperature. DADE® control sera I, II, III were also assayed. Values obtained are summarized in the above table.

Figure 2:
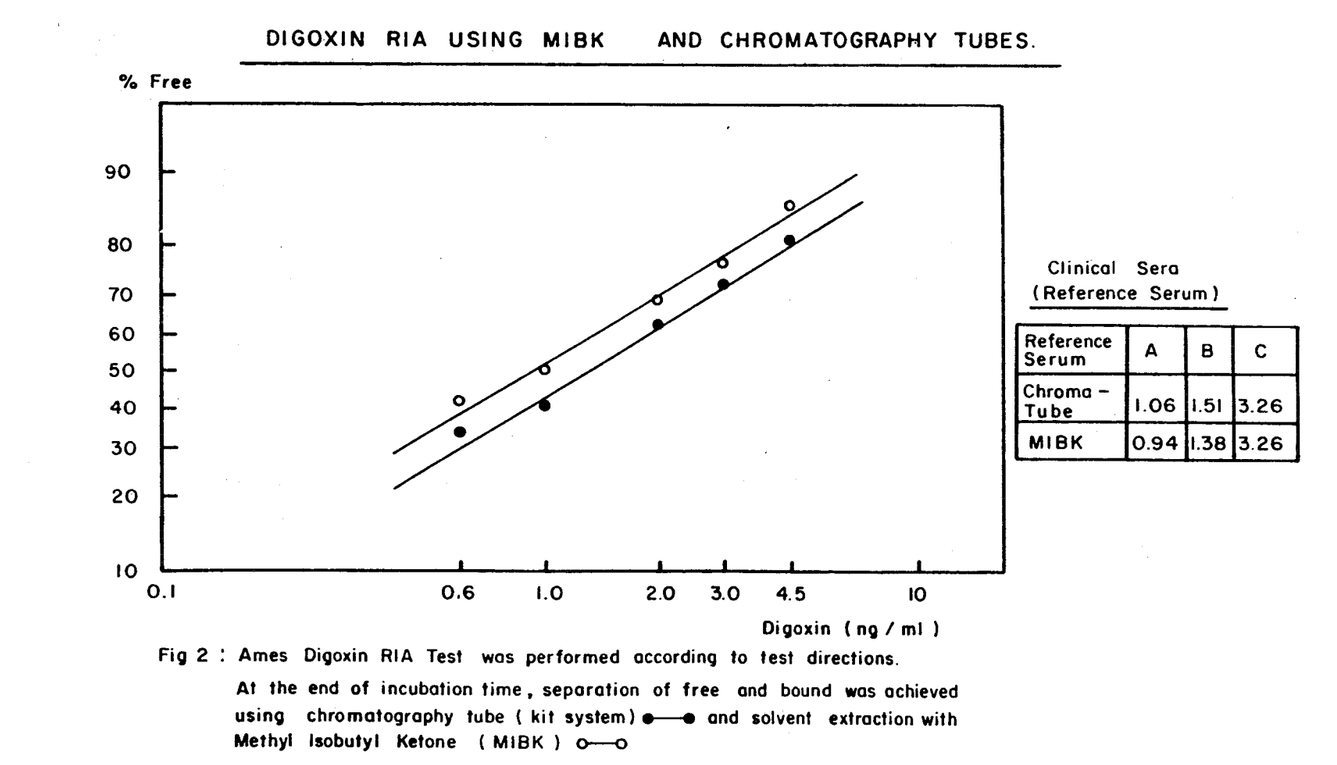

Fig 2: Ames Digoxin RIA Test was performed according to test directions.
At the end of incubation time, separation of free and bound was achieved using chromatography tube (kit system) ●——● and solvent extraction with Methyl Isobutyl Ketone (MIBK) ○——○

Figure 3:
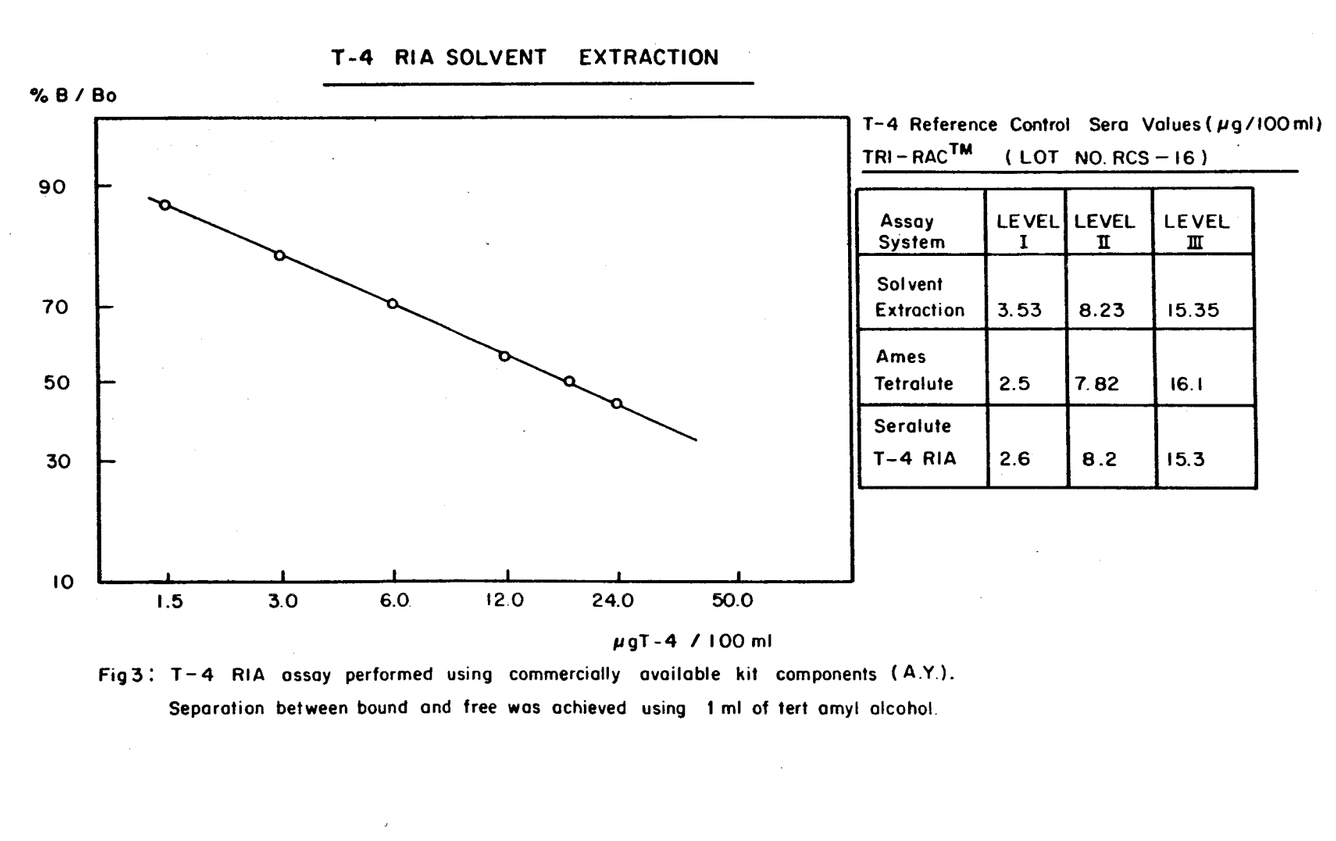

Fig 3: T-4 RIA assay performed using commercially available kit components (A.Y.). Separation between bound and free was achieved using 1 ml of tert amyl alcohol.

Figure 4:
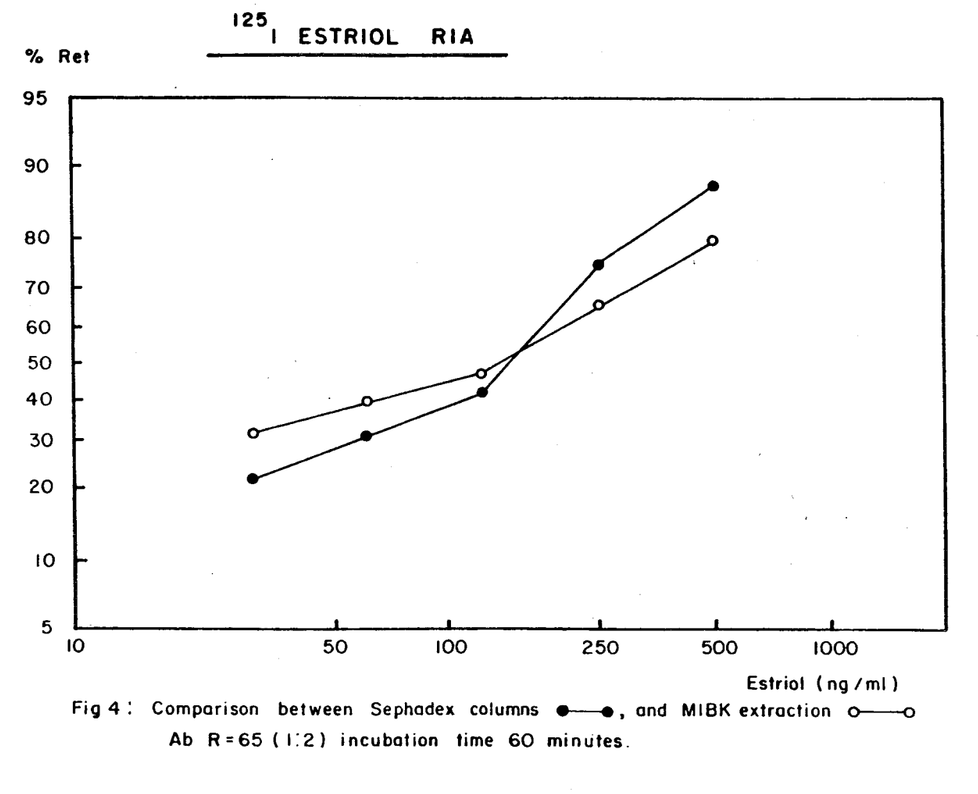

Fig 4: Comparison between Sephadex columns ●, and MIBK extraction ○
Ab R=65 (1:2) incubation time 60 minutes.

SPECIFIC BINDING ASSAY TECHNIQUE

This is a continuation-in-part application of pending Ser. No. 124,691, now abandoned.

The present invention relates to immunoassay technique. More specifically the invention relates to a simple, accurate and efficient operation to be applied in the specific binding assay techniques for separating the free ligand from the antibody-bound ligand.

As known, specific binding assays are based on the principle of monitoring specific binding reactions in which the extent of binding is a function of the unknown ligand present, by means of a labelled component. Among the known methods the following five specific binding assay techniques can be mentioned: Radioimmunoassay (RIA), metalloimmunoassay (MIA), free radical assay technique (FRAT), hemaglutination inhibition (HI) and enzyme multiplied immunoassay technique (EMIT). In the first two techniques, the mixture comprising the unlabelled ligand, labelled ligand and antibody is allowed to reach an equilibrium and the antibody-bound ligand is separated from the free ligand. In the radioimmunoassay, the ligand is labelled with a radioactive isotope, whereas in the metalloimmunoassay the ligand is labelled with a metal-containing reagent which contains also a suitable functional group by means of which one can attach the metal reagent to the hapten desired to be assayed. A full description of the latter is given in the U.K. Pat. No. 1,550,540 and corresponding U.S. Pat. No. 4,205,952.

The operation of separating the free fraction from the bound one, is of great importance and its accuracy determines the sensitivity and precision of the entire specific binding assay technique. In selecting and assessing a separation operation, it is useful to consider the criteria that should be fulfilled in order to obtain the desired result. The following major requirements of an ideal separation can be mentioned:

(a) A complete separation between the bound and free fraction should occur with a wide margin for error in the conditions used for separation. This implies that the method should not interfere with the primary binding reaction.

(b) The operation should be simple, quick and inexpensive, utilizing known reagents and available equipment.

(c) The operation should not be affected by the ligand utilized, since otherwise difficulties in standardization will be encountered. A number of separation operations can be found in the prior art and a brief description thereof is hereinafter presented:

Adsorption methods. Usually the free fraction is adsorbed; the adsorbents are commonly used for small peptides, steroid and thyroid hormones. The adsorption is determined by many factors, including the relative surface area of adsorbent, size and charge of antigen, nature and concentration of the competing proteins, temperature, ionic strength and pH. It is essential that the conditions for the use of the adsorption methods are optimized experimentally for each antigen. Examples of commonly encountered adsorbents are charcoal and silicates. The major problem is that always charcoal contains some unactivated material which has a high non-specific avidity for a wide range of substances, so that the bound fraction as well the free one may be adsorbed. In addition, charcoal may remove the bound antigen, particularly when a low-avidity binding agent is employed. The drawback of silicates is that the adsorption is dependent on the protein present, so that the optimal relative proportions of adsorbent and serum must be determined experimentally for each antigen.

Fractional precipitation with neutral salts or organic solvents which leaves in solution the free fraction. The forces that determine this effect are largely electrostatic and can be influenced by many factors such as temperature, pH, protein concentration and dielectric constant of the medium. Optimal conditions must be determined experimentally, with attention to the parameters of: pH, buffer, protein and salt concentrations. The applicability of these simple precipitations, depends mainly on the properties of the free antigen. Ammonium sulfate has been successfully employed in assays of plasma and urine extracts for many small peptides. Ethanol is perhaps more versatile, being suitable for a range of peptides. Polyethylene glycol has proved satisfactory for assays of insulin and may be useful for precipitation of peptide hormones which do not bind to standard adsorbents. All the methods described in this para suffer from the disadvantage that they require at least one centrifugation step.

Gel filtration. Since bound complexes are considerably larger in their molecular volume than the free antigens, they can be clearly separated by using an appropriate grade of a gel such as Sephadex. The gel has been used in two ways for phase separation; the incubate can be passed through a column under proper conditions such that the bound moiety is eluted, leaving the free moiety within the gel. A second method widely employed in competitive protein-binding technique is that of gel equilibration. The gel is present throughout the incubation and can be predispensed in equilibrium with the tracer binder solution. The free moiety within the pores of the gel is thus in equilibrium with that without. When the test sample is added to the gel suspension, equilibrium is rapidly reestablished, since the binding of tracer to gel is reversible. After allowing the gel particles to settle, a sample of the supernatant, which includes the bound fraction, can be removed and counted.

Paper chromatoelectrophoresis. A suitable paper is selected which adsorbs the free hapten at its site of application, while the bound fraction move from the origin under the influence of an electric current and buffer flow caused by evaporation. The disadvantage of this method is that it is too complex, time consuming and expensive to be used as a routine and also does not lend itself easily to automation. Also papers and antigens vary in their affinity characteristics which makes reproducibility difficult.

In view of the drawbacks of the above prior art methods it appears that it is a long felt need for an improved method of separating the free fraction from the bound fraction in the specific binding assay technique. The invention therefore consists in an improvement in the specific binding assay method for assaying a medium for a ligand, said method including the steps of:

(a) contacting said medium with reagent means which includes a labelled constituent comprising a conjugate of a labelling substance and a binding component and which forms with said ligand to be determined a binding reaction system producing a bound fraction and a free fraction of said labelled constituent, the quantity of labelling substance resulting in said bound fraction being a function of the amount of said ligand present in said ligand medium;

(b) separating said bound fraction from said free fraction; and (c) determining the quantity of labelling substance in either the bound fraction or the free fraction;

the improvement comprising providing as said labelled constituent a gamma labelled constituent; separating said bound fraction from said free fraction by a solvent extraction operation using an organic solvent having the property of selective extraction power toward the ligand and being only slightly water soluble or completely water insoluble and providing the formation of two phases; and determining the quantity of gamma labelled substances in either the bound fraction or the free fraction.

The method is applicable for any immunoassay technique (e.g. radioimmunoassay, free radical assay and metalloimmunoassay as described in the U.K. Pat. No. 1,550,540 and corresponding U.S. Pat. No. 4,205,952, which requires a separating operation between the bound and free fraction. Even though the general principles of solvent extraction have been well known for a long time, the use of solvent extraction for the separation of gamma-labelled constituent in the bound and/or free fractions has not been used in immunoassay techniques. The major reason for this lies in the expected interference of the solvent with the immunological reaction, either through damage caused to the specific binding protein by the solvent or through drastic changes caused by the solvent in the antibody-antigen equilibrium caused to the specific protein by the solvent or through drastic changes caused by the solvent in the antibody-antigen equilibrium reaction at the time of separating the bound and free fractions by the solvent extraction operation. It is therefore not surprising that the extensive literature on immunoassay techniques does not report any successful example of applying solvent extraction techniques for separating bound and free fractions in routine immunoassay techniques. The use of a scintillation liquid containing toluene has been suggested to extract tritium-labelled aldosterone by repeated operations for subsequent measurement in the scintillation counter, but the cumbersome procedure described (T. P. Jowett et. al., Clinical Science and Molecular Medicine, 1973, pages 607–623) did not indicate any possibility of general applicability.

In a recent book "Radioimmunoassay of Biologically active compounds" (C. W. Parker, Prentice Hall Inc. 1976, pages 68–71), it is mentioned that the determination of gamma-labelled constituents can be more efficiently performed than the beta-labelled constituents by an order of two to three fold. As pointed out therein:

. . . "the determination by gamma-labelling has several additional practical important advantages. Thus, their counting can be done in ordinary test tubes in well-type gamma counters, and transfer before counting is not necessary. The determination of beta-labelled constituents must be counted by liquid scintillation, which requires the use of expensive scintillation solutions and counting vials plus the expenditure of extra time in processing samples".

It is further mentioned that when an attempt is made to increase the marker specific activity by maximizing the number of beta-labelled radioactive atoms incorporated per molecule, rapid decomposition occurs. It is in particular interesting to point out that these Parker's statements are taken from several references all of them being dated prior to the above Jowett reference, but nevertheless Jowett in his review is suggesting the solvent extraction with toluene-scintillation liquid only for beta-labelled constituents.

It was therefore surprising and unexpected, when it was found according to the present invention that by the use of appropriate solvent and conditions, a general method could be devised for separating the bound and free ligands in immunoassays without adversely affecting either the binding ability of the binding protein or the binding protein-ligand equilibrium. Moreover the method according to the present invention can be of wide and general application to radioimmunoassay systems as well as to other immunoassays using non-isotopic labelling agents for marking the haptens to be analyzed. One of the advantages which characterizes the method according to the present invention is its versatility and the variety of configurations of the liquid-liquid system which can be applied for achieving the desired separation of free from bound ligand. In addition to the common liquid-liquid system, it can be envisaged various configurations in which the liquid-solvent and/or the aqueous medium of the immunological reaction are immobilized in a solid matrix. Thus the method would be applicable in a liquid-liquid system, a solid-liquid system and even a solid-solid system.

In a liquid-liquid system, the immunological reaction would be allowed to proceed in the usual manner in the aqueous medium. Following attainment of equilibrium in the reaction, an appropriate amount of a suitable solvent is added, and after a thorough mixing, the two phases are allowed to separate, the free ligand being transferred into the extracting solvent. The separation into zones takes place spontaneously, the bound and/or the free fraction being determined without actual separation of the aqueous and solvent phases into different vessels. This is an important advantage by itself, particularly for labelled radioactive elements since it decreases the number of operational steps. If deemed desirable to separate the aqueous and solvent phases, this can be done by any usual procedures, including the use of membrane systems.

Another configuration for separating the free from bound fraction is a solid-liquid system, in which the liquid is held in a solid matrix. After the immunological reaction is carried out in the usual manner in an aqueous solution and the required incubation period for attainment of equilbrium is allowed, an appropriate solvent is introduced and brought into intimate contact with the aqueous phase. After a thorough mixing, the two phases (aqueous and solvent) are allowed to separate, and an appropriate hydrophobic but solvent adsorbent material in the form of a strip, or other suitable form, is introduced into the reaction mixture. Adsorption of the solvent onto the solid material will carry with it the free ligand. The bound ligand in the aqueous phase and/or the free ligand adsorbed with the solvent onto the solid phase, can be measured by the appropriate analytical method chosen according to the type of labelling agent used for marking the hapten.

In a variation of the above configuration, the aqueous phase of the immunological reaction after the necessary incubation period, it passed through a porous cell, such as for instance through a porous spiral tubing surrounded by the solvent. By choosing the appropriate length of spiral tubing and the suitable solvent, on passage from one end of the tubing to the other end, all the free ligand will be extracted into the solvent leaving the aqueous phase to carry only the bound ligand. The free ligand extracted into the solvent cell and/or the bound ligand carried into the aqueous phase can be determined by a suitable analytical method chosen according to the labelling agent used to mark the hapten. The configuration just described is eminently suitable for automation of the whole procedure.

Another configuration is the use of solid-solid separation systems which provides additional versatility and great simplicity in supplying the present invention of solvent extraction for separation of bound and free ligands in immunological reactions. In this case the both liquids (solvent and immunological system) are held in two solid matrixes which may be different, or the same. For example a strip of suitable hydrophilic material is impregnated with the aqueous medium of the immunological reaction and the binding and ligands are adsorbed into this medium and allowed to incubate till equilibrium. A second strip of suitable hydrophobic material and impregnated with the appropriate solvent is brought into intimate contact with the first hydrophilic strip. Owing to the distribution of the reagents over the very large surface area of the two strips, the extraction of the free ligand from the hydrophilic strips onto the solvent in the hydrophobic strip will be extremely rapid and complete. Separation of the two strips will then allow for determining the labelled hapten in both the bound and free fractions. This configuration is also readily amenable to automation without requiring complicated auxilliary equipment.

Another simple configuration of the solid-solid extraction system for use with our invention consists in the preparation of two intertwining strips one made of hydrophilic and the other of hydrophobic material. The aqueous immunological reagents are added to the hydrophilic portion of the twinned-strip. After the necessary incubation period, the extracting solvent is added to the hydrophilic portion. This solvent will then rapidly migrate onto the hydrophobic portion. During this process of migration the solvent will exert its extraction operation thus conveying with it the free ligand onto the hydrophobic portion. Separation of the two intertwining strips will then allow for analysis of the bound and/or the free labelled ligand.

The method is also useful in enzyme immunoassay and particularly suitable in the case when the labelling agent is a fluorescent label, the measurements being carried out with a suitable spectrometer. When the labelling agent in the assay is a gamma-emitting radioisotope such as Iodine-125 and the upper phase is an organic solvent, the aqueous phase, after the solvent extraction will contain the antibody-antigen complex. Accordingly the lower phase will be determined by the gamma counter.

The method can also be used in the various kits available on the market for immunoassay, as appear from the experiments described in some of the Examples.

The method according to the present invention is also applicable in the separation of free antigen from bound antigen-antibody complex in the case of proteins, cells and other high molecular weight compounds if one uses two water soluble but mutually incompatible polymers to induce unmixing. This generates two aqueous phases between which various species may distribute. Such a phenomenon has been described in the literature (P. A. Albertson et. al, Nature, 184, 1465, 1959; G. Johanson et. al., Eur. J. Biochem., 33, 379, 1973). Incompatible pairs of polymers are numerous (see for example A. Dobry et. al., J. Polym. Sci. 2, 90, 1947). The method according to the present invention is technically simple, expeditious and inexpensive and should be considered as an ideal method in immunoassay technique. In order to enphasize the long felt need in the art for the technique described above, it would be worthwhile to quote from a well known specialist text-book "Principles of competitive protein-binding assays" (W. D. Odell and W. H. Daughaday, Editors), J. B. Lippincott Co., Philadelphia and Toronto, 1971, Chapter XI, page 303: "The fact that so many different separation techniques have been proposed is indication of some dissatisfaction with existing methods".

It appears that the technique according to the present invention comes nearest to the requirements of the ideal method than any of the existing prior art methods.

The method is useful in the specific binding assay method, for the detection of minute concentrations of chemical substances in biological fluids. From the known nomenclature of these chemical substances the following groups can be envisaged for their analysis:
  Alkaloids, such as: morphine, codeine, dihydrocodeine, heroin, oxymorphone, metopon, pholcodine, etc.
  Barbiturates, such as: Veronal, luminal, seconal, phenobarbital, barbital, etc.
  Steroids, estrogens such as: $\beta$-estradiol, estrone, estriol, 17$\alpha$-ethyinyl estradiol etc., androgens, progestogens; adrenocortical hormones, etc.
  Cannabinoids and their matabolites.
  Vitamins, such as: Carothene, riboflavine, thiamine, niacin, ascorbic acid, tocopherol, phytyl-1,4,-naphtoquinone, etc.
  Amino acids and polypeptides
  Sugars, including saccharides and polysaccharides.
  Tranquilizers, such as: meprobamate, valium, oxazepam, phenotiazines, etc.

In addition to the above haptens, other miscellaneous compounds such as cocaine, prostaglandin, aantibiotics such as penicillin, chloromycetin, actinomycetin and nucleic acids and nucleotides; insecticides, fungicides, bacteriocides and nematocides such as malathion, carbamates, etc. can also be assayed with the method according to the present invention. In general, antigens, haptens and their antibodies, hormones, vitamins, drugs, metabolites and their receptors and binding materials may be determined using the present method.

Among the particular constituents to be determined the following can be mentioned:
  Compensated $T_4$; $T_3$ Uptake;
  Cortisol; Insulin;
  Digoxin; Triiodothyronine;
  Folate; Thyroxine (Total $T_4$);
  hGH; TSH;

The organic solvents useful for the present invention must fulfil the following requirements:

(a) It should be slightly water miscible or completely water immiscible.
(b) It must possess a marked selective extraction power towards the antigen.
(c) Does not have any specific interference with any constituent of the system.

Organic solvents to extract antigen as such are very numerous and most of them are unsuitable for the present invention. Thus all organic solvents that have complete or very marked miscibility with water cannot be used e.g. ethanol, acetone etc. However the present literature is fortunately abundant with a large number of organic solvents which possess indeed the above criteria. Generally the organic solvents will be selected from hydrocarbons, halohydrocarbons, oxygen derivatives of hydrocarbons, nitrogen derivatives of hydrocarbons, phosphorus derivatives of hydrocarbons in which the hydrocarbon moiety can vary from $C_3$ to $C_{20}$. Typical examples of such organic solvents are: methyl isobutyl ketone, chloroform, dichloromethane, carbon tetrachloride, tert amyl alcohol, benzyl alcohol, ethyl acetate, tert-butyl methyl ether, hexane, heptane, isooctane etc. The choice of the preferred solvent for each system is made by carrying out a simple experiment in each case as illustrated hereinafter.

In the following Table 1, there are illustrated the data of some of the useful solvents in respect to the criteria mentioned hereinbefore in an experiment to choose an adequate solvent for estriol. $^{125}I$ estriol was selected as ligand tested for its extraction in the presence of 250 ng/ml unlabelled estriol and without it.

TABLE 1

| Solvent | % Estriol extracted Tracer only | with 250 ng/ml | % solubility in water |
|---|---|---|---|
| Methyl isobutyl ketone | 91–94 | 90–94 | 1.9 |
| Ethyl acetate | 90–94 | 90–92 | 3.3 |
| Triethyl amine | 86–91 | 86–90 | 1.5 |
| Benzyl chloride | 78–80 | 76–78 | 0.05 |
| Tert-amyl alcohol | 78–82 | 80–85 | 12.5% (separated only after centrifugation) |
| Chloroform | 52–53 | 53–54 | 1.01 |
| Dichloromethane | 45–47 | 52–51 | 2 |
| Carbon tetrachloride | 35–38 | 38–40 | 0.08 |

It should be pointed out that organic solvents suitable to extract gamma-labelled constituents, are not useful for determining beta-labelled constituents in the scintillator liquid. Thus for instance when using methyl isobutyl ketone as solvent, and extracting phenobarbital labelled with tritium, it was found that the presence of the solvent in the toluene-based liquid scintillator caused a sharp decrease in the efficiency of counting the radioactivity even below 40% as mentioned by Parker in his book. Actually even Jowett et al in his review on determination of beta-labelled constituents using toluene-based liquid scintillation does mention that this technique is likely to cause protein-denaturation (page 620).

The method of separation according to the present invention will be hereinafter illustrated with estriol digoxin and T-4 taken as ligands, and the results obtained are compared with the known chromatographic column or precipitation methods.

EXAMPLE 1—Solvent extraction method for Digoxin RIA

Materials and methods

After the incubation time, the appropriate amount of solvent was added into each test tube (polypropylene), test tubes were capped and vortexed for 30 seconds (or all test tubes together were shaken vigorously by inverting them for 2 minutes). All test tubes were left to stand for a few minutes (5–10) and half of the amount of the solvent (or the aqueous) solution was transferred to new test tubes for counting.

Experiments were also carried out in order to avoid the "physical" separation (transferring a definite volume after phase separation).

A copper shielded well liner was used to cover the upper phase (usually the solvent) and each test tube was inserted into the gamma-counter so that only the lower part of the test tube (containing the aqueous phase with the bound fraction) could be counted. Digoxin kit components were reconstituted according to kit directions for use.

Reaction mixture included 200 μl antiserum (lot no. 9002), 400 μl of $^{125}I$ Digoxin derivative (lot no. 9007), 100 μl of standards (lot no. 9902) or control sera (DADE three level control sera) all kit components contained EDTA phosphate buffer (pH 7.4±0.1). Reaction was carried out for 30 minutes at room temperature and 2 ml of methyl isobutyl ketone were added to each test tube and vortexed for 30 seconds. Separation was achieved within 5–10 minutes and the aqueous phase was counted on a GAMMACORD II (trademark of Ames Yissum Research Laboratories) using a shielded well liner (15 mm spacer).

RESULTS AND CONCLUSIONS

The attached FIG. 1 represents the standard curve obtained, plotted as logit bound/total (B/T) versus log Digoxin concentration. Total delta % retention (slope between 0.54 and 4.6 ng/ml) is 50%. Control sera values (FIG. 1) indicates good correlation with commercially available kits for digoxin determination.

FIG. 2 represents a comparison of solvent extraction with chromatographic tubes method.

EXAMPLE 2—Solvent extraction method for T-4 RIA. (T=thyroxine)

Materials and methods $^{125}I$-T-4 lot no 0047 containing 3 mg/ml 8-anilino-naphthalene sulfonic acid (ANS) in Tris-Maleate buffer pH 7.3±0.1 (Tris 1.47 g, Maleic Acid 0.62 g. Disodium EDTA 0.22 g) in 150 ml of doubly-distilled water.

Antiserum lot no. 0007 reconstituted with same buffer. T-4 standards prepared in buffer solution, reaction mixture included 200 μl of reconstituted $^{125}I$-T-4.50 μl standards or serum samples and 400 μl of antiserum was incubated for 30 minutes at room temperature. Three control sera (sera produced by Dade Division of American Hospital Supply Corp. and sold under the trademark TRI-Rac-lot no. RCS-16) level I, level II and Level III were also assayed with the standard curve.

After the incubation, 200 μl of saturated solution of $(NH_4)_2SO_4$ and 1 ml of tert-amyl-alcohol were added to each test tube. All test tubes were capped and rotated (upside down) for two minutes. The aqueous phase was counted on GAMMACORD II (γ counter) using a shielded well liner (no physical separation was required).

RESULTS AND CONCLUSIONS

Results were calculated as % Bound over Bound Zero (B/Bo), and are represented in the attached graph (FIG. 3), Control sera values were calculated and also are represented. These values are compared to the values obtained by the Ames T-4 kits (kits produced by Ames Yissum Research Laboratories and available under the trademarks Tetralute and Seralute T-4 RIA).

From the results obtained, it can be seen that the slope between the 1–5 mcg/dl standard and the 24 mcg/dl standard is 43%.

The control sera values correlate well with the values obtained with the commercial kits. This implies that the system can distinguish between normal and hyperthyroid, and hypothyroid values.

EXAMPLE 3—SOLVENT EXTRACTION method for Estriol RIA

Materials and methods

Buffer:

Estriol RIA system was carried out in EDTA phosphate buffer (0.01M, pH 7.4).

Antisera:

Two different sources of antisera used:

(1) antiserum which was produced by rabbits injected with Estriol 6-0 carboxymethyl BSA (R-68, obtained from Ames Yissum Research Laboratories used as crude antiserum).

(2) Antisera which were produced by rabbits injected with Estriol-3-0BSA R-63, R-64, R-65, produced at the Technion, Haifa, and used as purified Immunoglobulins) 36% ammonium sulfate precipitation.

Estrogen Tracers:

$^{125}$I-Estriol produced at the Ames-Yissum Laboratories. $^3$H Estriol purchased from New England Nuclear (N.E.N.) $^3$H Estrone and $^3$H Estradiol also purchased from N.E.N.

Estrogen and Estrogen derivatives:

Estriol (Merck), Estradiol (Sigma), Estrone (Sigma), Estriol-3-0 Carboxymethyl (produced at Technion).

A. Standard Curve Determination

100 μl of tracer in EDTA phosphate buffer (containing 0.2% polyvinyl alcohol, P.V.A.), 200 μl of Estriol standard (in the same buffer) and 100 μl of antiserum (using the appropriate dilution) were incubated for 60–90 minutes at room temperature.

After the incubation time, the Estriol bound was separated from the free using different separation methods and the radioactivity of the free fractions was determined. Standard curve was plotted as a free versus log Estriol concentration (ng/ml).

B. Separation Methods

1. Sephadex Columns—Reaction Mixture (200 μl) was applied on top a G-10 Sephadex (trademark of Pharmacia AB, Sweden, for absorption columns) column and left to penetrate into the column. Columns were then washed with 3 ml of EDTA phosphate buffer to remove the bound fraction.

2. Solvent Extraction

After the incubation, 200 μl of the reaction mixture were extracted with 400 μl of solvent (see results) by vortexing 30 seconds (using polypropylene, plug-stoppered test tubes). After phase separation, 200 μl of the solvent were transferred to test tubes and counted.

RESULTS AND CONCLUSIONS

The solvent extraction method results were calculated as % free over log estriol concentration and are represented in FIG. 4. These values are compared with the results obtained in the separation of the bound and free fractions on Sephadex columns. As can be seen from this comparison the solvent extraction method with RIA can be used to determine estriol in biological fluids.

EXAMPLE 4—Solvent extraction method for Digoxin RIA

A similar experiment as in Example 1 was carried out with the commercially available Digoxin RIA kit supplied by Becton Dickinson. All kit components were used unchanged except for the $^{125}$I-Digoxin tracer which was prepared specially for this experiment by Becton Dickinson research laboratory, so that the appropriate amount of radioactivity was contained in 0.1 ml portions instead of 1 ml portions as provided in the original kit.

DADE Control sera (I, II and IV) were reconstituted and assayed together with the kit, according to the kit instructions. After the prescribed incubation time, 1.0 ml of t-amyl alcohol was added to each tube, vortexed to extract the free digoxin and after phase separation, 150 μl of the aqueous phase were transferred for radioactivity counting. The results obtained for the standard curve (expressed as % B/Bo) and those for the control sera (expressed as % B/Bo and mg Digoxin/ml) are summarized in Table 2 below:

TABLE 2

| Digoxin (ng/ml) | B/Bo (%) | DADA CONTROL | SERA % B/Bo | ng/ml Found | Digoxin Expected |
|---|---|---|---|---|---|
| 0.5 | 74.0 | Level I | 61.1 | 0.72 | 0.71–1.06 |
| 1.0 | 49.0 | | | | |
| 1.5 | 35.0 | Level II | 32.3 | 1.78 | 1.55–2.17 |
| 2.0 | 27.5 | | | | |
| 3.0 | 20.0 | Level III | 20.2 | 2.90 | 2.64–3.49 |
| 5.0 | 12.0 | | | | |

EXAMPLE 5—Solvent extraction method for RIA-Estradiol 17β

A commercially available ($^3$H) RIA kit for estradiol supplied by Isopac was tested by the solvent extraction method as follows:

All kit components were prepared according to kit directions. One experiment (A) was carried out exactly according to the kit protocol. A second, parallel experiment (B) was performed according to kit protocol up to, and including, the incubation step. After incubation time in experiment B, 1.6 ml of solvent (a 1:1 mixture of tert-amyl alcohol and tert-butyl methyl ether, presaturated with assay buffer) were added to all tubes and vortexed for 20 seconds. After phase separation (about 10 minutes) the upper solvent phase, containing the free estradiol, was transferred to scintillation vials to which 5 ml of scintillation liquid (Instagel II, trademark of Packard) were added and the radioactivity determined. Table III below presents the results calculated as % B/Bo for the two parallel experiments. When plotted on a logit-log graph paper according to kit directions, a linear plot is obtained for both experiments, but the results of experiment B (using the solvent extraction procedure) exhibit a steeper standard curve thus allowing for a more sensitive assay.

TABLE 3

| Estradiol standards pg/ml | % B/Bo Expt. A (kit) | % B/Bo Expt. B (solvent extn.) |
| --- | --- | --- |
| 12.5 | 96.0 | 98.0 |
| 25.0 | 89.0 | 89.0 |
| 50.0 | 85.0 | 76.0 |
| 100.0 | 59.0 | 40.0 |
| 200.0 | 40.0 | 23.0 |
| 400.0 | 21.0 | 14.0 |

EXAMPLE 6—Solvent extraction method for RIA-phenobarbitone

The components used for a phenobarbitone RIA were a ($^3$H) phenobarbitone tracer (N.E.N), a phenobarbitone antiserum R-66X (Technion) and tris-maleate assay buffer (pH 7.3, 0.078M Tris, 0.035M maleic acid) containing 0.1% PVP (polyvinyl pyrrolidone).

The tracrer, 100 µl (approx. 10 nono Ci/tube) was added to test-tubes followed by the addition of 50 µl phenobarbitone standards and 100 µl of diluted antiserum. All test-tubes were incubated overnight at 4° C. After incubation, 0.5 ml of solvent (tert-butyl methyl ether, TBME in one experiment and, MIBK in a parallel experiment) were added to each assay tube and vortexed for 20-30 seconds. After phase separation on standing, the aqueous phase was transferred to scintillation vials for radioactivity determination. The following Table 4, summarizes mean values (of duplicates) expressed as % B/Bo.

TABLE 4

| Phenobarbitone standards ng/ml | TBME (tert-butyl methyl ether) | % B/Bo MIBK (methyl isobutyl ketone) |
| --- | --- | --- |
| 5 | 96.5 | 73.0 |
| 10 | 79.0 | 63.0 |
| 25 | 52.0 | 45.0 |
| 50 | 30.0 | 30.0 |
| 100 | 23.0 | 19.0 |

EXAMPLE 7—Solvent extraction method for RIA-THC

An assay using the solvent extraction method was developed for tetrahydrocannabinol (THC) metabolites using a ($^3$H)-THC tracer (Amersham). All assay components were prepared in tris-maleate buffer (pH 7.3) containing 0.2% PVP and 0.1% Triton X450 (trademark of Rohm and Haas). The ($^3$H)-THC tracer, 100 µl, was mixed with 50 µl of THC standards and 100 µl of diluted anti-THC antiserum, R-41Va (prepared at the Technion) and incubated overnight at 4° C. Three experiments were carried out in parallel. In one experiment the separation of the free and bound fractions was carried out by the dextran-coated charcoal method and the other two experiments used the solvent extraction method, tert-amyl alcohol in one and MIBK in the other. The solvent, 500 µl, was added to the assay tubes and vortexed for 20-30 seconds. After phase separation (10-20 minutes) 150 µl of the aqueous phase were transferred to scintillation vials for radioactivity determination. The following Table 5 summarizes the results, expressed as % B/Bo for the three experiments.

TABLE 5

| THC standards ng/ml | t-amyl alcohol | % B/Bo MIBK | Charcoal |
| --- | --- | --- | --- |
| 1 | 90 | 98 | 98 |
| 2 | 86 | 84 | — |
| 4 | 77 | 68 | 86 |
| 10 | 36 | 30 | 55 |
| 20 | 15 | 18 | 32 |
| 40 | 6 | 8 | 21 |

We claim:

1. A specific-binding assay method for assaying a ligand in an aqueous medium, comprising the steps of:
   (a) preparing a mixture of said aqueous medium with a reagent containing a labeled constituent, which constituent comprises a conjugate of (i) a gamma-labeling substance and (ii) a binding component which binds said ligand, to form a bound fraction and a free fraction of said labeled constituent, the quantity of said labeling substance in said bound fraction being proportional to the amount of said ligand in said aqueous medium;
   (b) then contacting said mixture with a solvent medium which (i) has the property of selective extraction power toward said ligand and (ii) forms a separate phase from said aqueous medium, such that said free fraction is extracted into said separate phase; and thereafter
   (c) determining the quantity of said gamma-labeling substance in either said bound fraction of said free fraction,
wherein said solvent medium consists essentially of at least one selected from the group consisting of methyl isobutyl ketone, chloroform, dichloromethane, carbon tetrachloride, tert-amyl alcohol, benzyl alcohol, ethyl acetate, tert-butyl methyl ether, hexane, heptane and isooctane.

2. A method according to claim 1, wherein said solvent medium consists essentially of tert-amyl alcohol and tert-butyl methyl ether.

3. A method according to claim 1, wherein step (c) is carried out while said organic phase is in contact with said aqueous medium.

4. A method according to claim 1, wherein step (c) comprises determining the quantity of said gamma-labeling substance in said bound fraction.

5. A method according to claim 1, wherein said ligand is an antigen or hapten and said binding component is an antibody which reacts selectively with said antigen or hapten.

6. A method according to claim 1, further comprising after step (b) a step (d) of contacting said solvent medium with a solid, hydrophobic material which adsorbs said solvent, whereby said free fraction is taken into said solid material.

7. A method according to claim 1, wherein step (a) comprises impregnating a solid, hydrophilic material with said mixture, such that the binding of said ligand by said binding component proceeds to equilibrium in said hydrophilic material; and step (b) comprises contacting said hydrophilic material with a solid, hydrophobic material impregnated with said solvent.

8. The method according to claim 1, wherein said ligand is selected from the group consisting of a hormone, a barbitutrate, a steroid, a vitamin, a tranquilizer, a drug, and an alkaloid.

9. The method according to claim 8, wherein said ligand is Digoxin.

10. The method according to claim 8, wherein said ligand is Estriol.

11. The method according to claim 8, wherein said ligand is Thyroxine (T-4).

12. The method according to claim 8, wherein said ligand is Estradiol 17β.

13. The method according to claim 8, wherein said ligand is Phenobarbitone.

14. The method according to claim 8, wherein said ligand is Tetrahydrocannabinol.

* * * * *